United States Patent [19]

Stratmann et al.

[11] Patent Number: 5,369,370

[45] Date of Patent: Nov. 29, 1994

[54] METHOD AND APPARATUS FOR THE MEASUREMENT OF THE CORROSION POTENTIAL BETWEEN A COATED METAL SURFACE AND A REFERENCE ELECTRODE

[75] Inventors: Martin Stratmann, Meerbusch; Heinz Streckel, Mettmann, both of Germany

[73] Assignee: Max-Planck-Institut fuer Eisenforschung GmbH, Duesseldorf, Germany

[21] Appl. No.: 835,933

[22] PCT Filed: Jun. 12, 1991

[86] PCT No.: PCT/EP91/01093

§ 371 Date: Mar. 10, 1992

§ 102(e) Date: Mar. 10, 1992

[87] PCT Pub. No.: WO91/19972

PCT Pub. Date: Dec. 26, 1991

[30] Foreign Application Priority Data

Jun. 13, 1990 [DE] Germany ............... 4018993

[51] Int. Cl.$^5$ ............................ G01R 31/02
[52] U.S. Cl. .................. 324/663; 324/458; 324/158.1
[58] Field of Search .......... 324/458, 457, 71.2, 324/71.1, 663, 686, 683, 658, 72, 72.5, 681, 682, 661, 158 D

[56] References Cited

U.S. PATENT DOCUMENTS

| | | |
|---|---|---|
| 3,857,095 | 12/1974 | Mitchie et al. ............... 324/662 |
| 3,906,783 | 9/1975 | Schumacher ................ 324/725 |
| 4,067,225 | 1/1978 | Dorman et al. ............... 324/662 |
| 4,072,896 | 2/1978 | Bijlmer ........................ 324/61 P |
| 4,393,348 | 7/1983 | Goldstein et al. ............ 324/158 D |
| 4,433,288 | 2/1984 | Moore ........................... 324/158 D |
| 4,481,616 | 11/1984 | Matey ........................... 369/58 |
| 4,649,336 | 3/1987 | Binder et al. .................. 324/458 X |
| 4,812,756 | 3/1989 | Curtis et al. .................... 324/158 D |
| 5,065,103 | 11/1991 | Slinkman et al. .............. 324/458 |
| 5,136,247 | 8/1992 | Hansen .......................... 324/457 |
| 5,216,362 | 6/1993 | Verkuil ......................... 324/158 D |

FOREIGN PATENT DOCUMENTS

| | | |
|---|---|---|
| 2346834 | 10/1977 | France . |
| 2607935 | 6/1988 | France . |
| 2160963 | 6/1973 | Germany . |
| 3236112 | 7/1986 | Germany . |

OTHER PUBLICATIONS

J. Phys. E: Sci. Instrum., vol. 21 (1988), pp. 147–151 Scanning Capacitance Microscopy; C. D. Bugg, et al.
Ber. Bunsenges. Phys. Chem. 92, pp. 1244–1250 (Dec. 1988); Stratmann, et al. The Investigation of the Corrosion of Metal Surfaces, Covered with Thin Electrolyte Layers–A New Experimental Technique.
Journal of Physics E/Scientific Instruments 21 (1988) Jul., No. 7, Bristol, Gr. Britain, pp. 674–679; Design and Performance of a Kelvin Probe for the Study of Topographic Work Functions.
J. Phys. E: Sci. Instrum., vol. 17, Dec. 1984, L. B. Harris, et al. pp. 788–792; Vibrating Capacitor Measurement of Surface Charge.
J. Phys. E: Sci. Instrum. 21 (Dec. 1988) C. D. Bugg, et al., pp. 147–151, Scanning Capacitance Microscopy.

*Primary Examiner*—Maura K. Regan
*Attorney, Agent, or Firm*—Nields & Lemack

[57] ABSTRACT

Method for the investigation of the condition of a corrodible surface coated with a polymer, wherein the corrosion potential at the corrodible surface is measured without contacting either the corrodible surface or the polymer coating by means of a Kelvin probe which measures the potential between the corrodible surface and a probe electrode. The potential difference reflects the corrosion potential and, thus, the corrosion condition of the polymer coated surface.

2 Claims, 2 Drawing Sheets

METHOD AND APPARATUS FOR THE MEASUREMENT OF THE CORROSION POTENTIAL BETWEEN A COATED METAL SURFACE AND A REFERENCE ELECTRODE

The present invention relates to a method and apparatus for the investigation of the condition of a metal surface, which is provided with a coating, especially of a dielectric material, such as a polymer.

An increasingly greater technical significance is being given to polymer coatings of reactive metal surfaces. They serve as protection of useful metals such as iron, zinc or aluminum against corrosion, they serve as insulating cover layer with special dielectric constructive characteristics as in the case of adhesives.

The technical demands of such connecting systems upon coatings, especially polymers on metal substrates, are a high mechanical stability of the phase-boundary as well as a high corrosion-protection of the substrate against aggressive media by means of the applied coating. The failure of the bond between metal and coating is very often based upon the diffusion of components of particles of corrosive media through the coating, the accumulation of water and ions at the metal/coating interface in first monomolecular and then three-dimensional thick films, the possible formation of an electrochemical double layer, the following corrosion reactions, and finally a large scale delamination of the coating caused by the electrochemical reaction. Principally components of a corrosive medium may diffuse through the coating to the substrate/coating interface, but they may also reach the locally unprotected metal directly along local defective places, e.g. pores or local damages, and from there spread out along the phase-boundary. Such undermining and release, which spreads out from local defects and blemishes, is of particular significance. There is no doubt that in this process electrochemical reactions of the phase-boundary between metal and coating are of great significance and that e.g. a cathodic polarization of the phase-boundary accelerates the delamination velocity significantly. It is also known that the rate of the electrochemical reactions is strongly determined by the diffusion of ions through the layer, such as a polymer film. Finally it is known that reactions in inorganic conversion layers in certain cases are the cause of the loss of adhesion of the coating.

The technical significance of the delamination of the coatings, especially polymer films, is reflected in countless industrial corrosion tests, in which very often the delamination starting from a mechanical injury after corrosion at the free corrosion potential (salt spray test, etc.) or during a cathodic polarization (potentiostatic or galvanostatic holding test) is measured. These tests are regarded as one basis for the development of new coating methods or coating materials. It is at any rate extremely difficult to determine the delamination rate directly and in the shortest possible time.

As possible techniques up to now optical measurements are used in order to determine the delaminated distance (counting bubbles, formation of rust) or the delaminated lacquer is removed mechanically be scratching or by adhesive strips. It is disadvantageous that the valuation in both of these known methods is not free from uncertainty; the methods do not permit a continuous measurement of the delmaination rate; the mechanical testing of the delamination is not nondestructive and finally both methods are only useable when a noticeable destruction of the metal/coating phase-boundary has already occurred. Short-term tests with high resolution are hence not possible.

Electrochemical methods for investigating the delamination rate (e.g. impedance spectroscopy) are also known; however, they have up to now not shown unambiguous results.

The formation of delaminated zones under an intact polymer layer, i.e. far distant from an injury, has up to now only been possible to investigate with the help of an ultrasonic microscope. This method is nevertheless very expensive and is not well suitable in cases, in which the substrate is coated with multiple layers, as is frequently the case in modern lacqueres and coatings.

The present invention, accordingly, addresses the task, starting from this state of the art, of providing a method and an apparatus for investigating the condition of a metal surface which is coated with a solid dielectric material (typically a polymer or synthetic material) and which is not directly accessable. The method should be able to determine quickly and reproducibly even very small changes of the metal surfaces, such as the first beginning of the corrosion and delamination processes.

This task is solved in accordance with the invention of a method in which the corrosion potential between the coated metal surface and a vibrating reference electrode (Kelvin probe) is measured without contact.

An apparatus according to the invention includes a Kelvin probe (i.e. an oscillating condenser).

The method and the apparatus according to the invention makes possible the measurement of corrosion potentials underneath coatings, such as polymer films, with high spatial resultion as well as quickly and reproducably.

The principle of the Kelvin probe has long been known and in the past has been used primarily for the measurement of work functions: If two different metals are conductively connected with each other, electrons flow from one metal into the other, until a balance of the Fermi levels has taken place. By means of the electron transfer, a voltaic potential difference is produced between both metals. If one now allows one metal to oscillate with respect to the other, there results at constant voltaic potential difference an alternating current in the conductive connection between the two metals, since the capacitance between the two metals changes with the oscillation. If an additional voltage source is connected between the two metals, the Fermi levels can be shifted in such a way that no excess charge exists any more in the metals. Then the alternating current is zero and the value of the applied voltage is equal to the voltaic potential difference.

It is also already known that corrosion potentials of essentially free metal surfaces can be measured by means of a Kelvin probe (Bet. Bunsenges. Phys. Chem. 92, 1244–1250 (1988)). Yet in the present invention this technique is not used to measure the work function of a metal or the corrosion potential of an essentially free metal surface, but rather the electrode potential at the metal/coating interface below a dielectric coating. By way of the voltaic potential difference measured with the aid of a Kelvin probe, one can calculate the electrode potential or corrosion potential, respectively, at a not-directly-accessible metal surface, which is covered with a solid dielectric coating, if the work function of the reference metal and the dipole-potential of the surface under investigation have been determined by way of standard measurements with standard metal/metalion reference electrodes. This is possible in practice without greater difficulties.

The present method and the present apparatus offer, among others, the following advantages:

They allow a nondestructive investigation of corrosion processes beneath intact polymer films.

They allow a continuous tracking of the undermining and delamination of dielectric layers, especially polymer films, without disturbing the corrosion reaction.

They make possible a short-time test, since the delamination may be determined with high spatial resolution and therefore is detected in an early stage.

They allow a quantitative investigation of the delamination of polymer films, which is free from uncertainty.

They allow the recognition of corrosion damage beneath intact polymer films in a very early stage; long before an optical observation allows recognition of damage.

The following practical uses are possible, among others:

Investigation of the delamination of lacquer films starting from injuries (Standard-Test of the lacquer industry).

Investigation of the influence of metal pre-treatment (phosphatizing, chromatizing, etc.) on the delamination rate.

Investigation of the influence of additives in the lacquer (pigments, inhibitors) on the delamination rate.

Investigation of the influence of a polarization of the metal surfaces (cathodic protection, zinc-treated steel plate) on the delamination rate.

Besides the delamination rate, which results from the potential profile, it is also possible to determine possible corrosion reactions from the absolute potential value. Thus e.g. phosphated steel surface may also be undermined by water, while the surface shows no corrosion by virtue of the passivating phosphate layer.

In the following, the invention will be explained in greater detail with reference to the drawings, in which.

Figure 1:
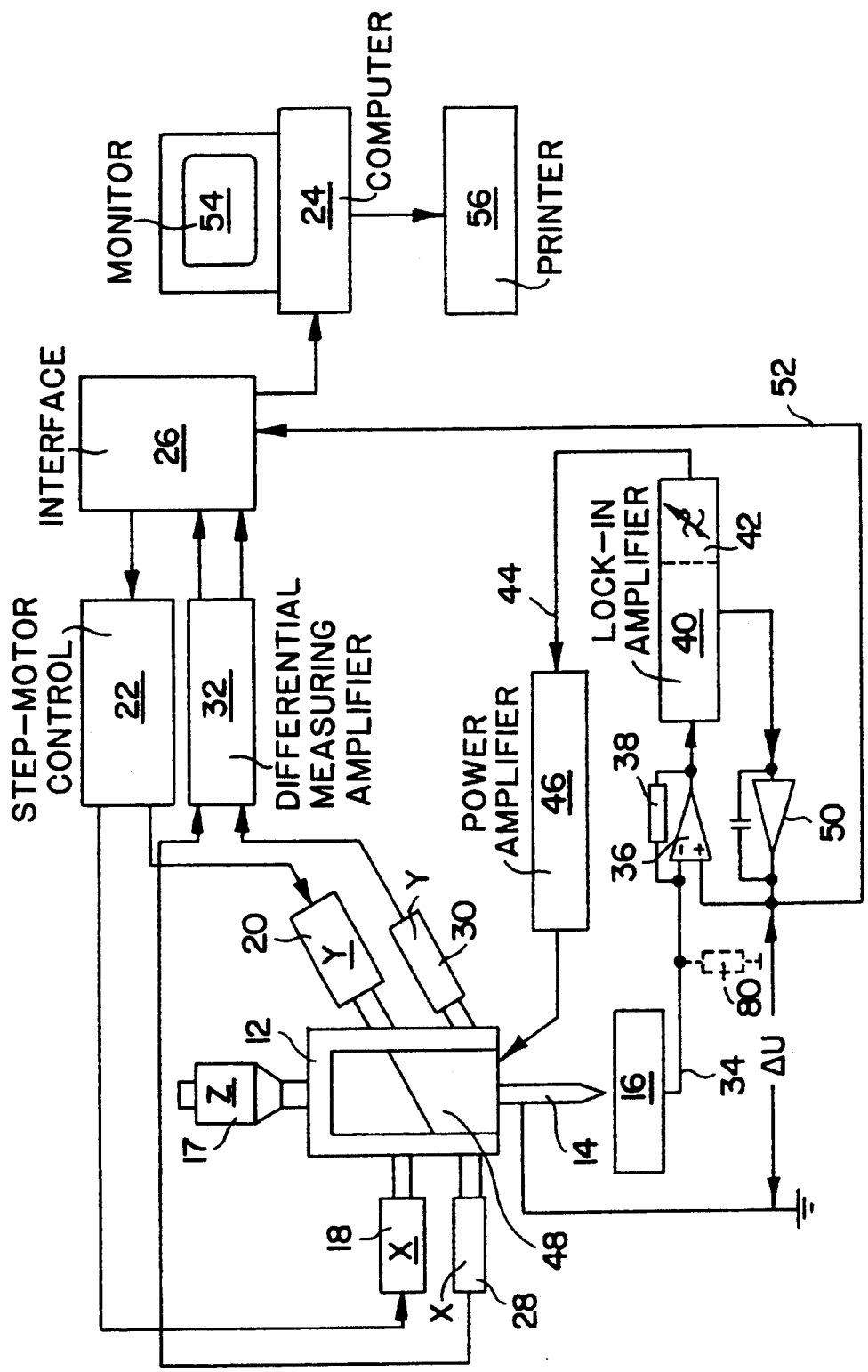
FIG. 1 shows a schematic block representation of an apparatus for investigation of the condition of a coated metal surface according to a preferred embodiment of the invention.

The apparatus shown in FIG. 1 includes a measuring system 10 which includes a measuring head 12 for the vibrating support of a reference electrode ("Kelvin probe") 14 and serves for the positioning of the reference electrode in relation to a coated surface of an object to be investigated (sample) 16. The measuring system and the measuring head will be explained in still greater detail with reference to FIGS. 2 and 3. A micrometer screw 17 serves for the positioning of the reference electrode 14 (which shows the form of a rod running to a tip or a needle) in the Z direction. For the positioning of the reference electrode 14 in an X-Y plane parallel to the sample's surface one provides an X-step motor 18 and a Y-step motor 20, which are connected to a step-motor control 22, which in turn is controlled by a computer 24 via an interface 26. For reading position there are provided an X-coordinate meter 28 and a Y-coordinate meter 30, the position output signals whereof are led to the computer 24 via differential measuring amplifier 32 and the interface 26.

The metallic object to be investigated 16 is held by an insulated holder (not shown in FIG. 1) and coupled via a line 34 with the minus input of a differential amplifier 36 the output whereof is coupled via a decoupling resistance 38 with the plus input and also with a signal input of a lock-in amplifier 40. The lock-in amplifier includes a variable-frequency a-c voltage generator 42, which delivers a variable-frequency operating voltage for the amplifier part and via an output line 44 and a power amplifier 46 a control voltage for a magnet coil 48 in the measuring head 12.

The signal output of the lock-in amplifier 40 is coupled with the input of an integrator 50. The output of the integrator is connected on the one hand with the plus input of the differential amplifier 36 and on the other hand with a measurement-signal input of the interface 26 via a line 52. The computer 24 is coupled with a monitor 54 and a printer 56, which serve as output apparatus.

Figure 2:
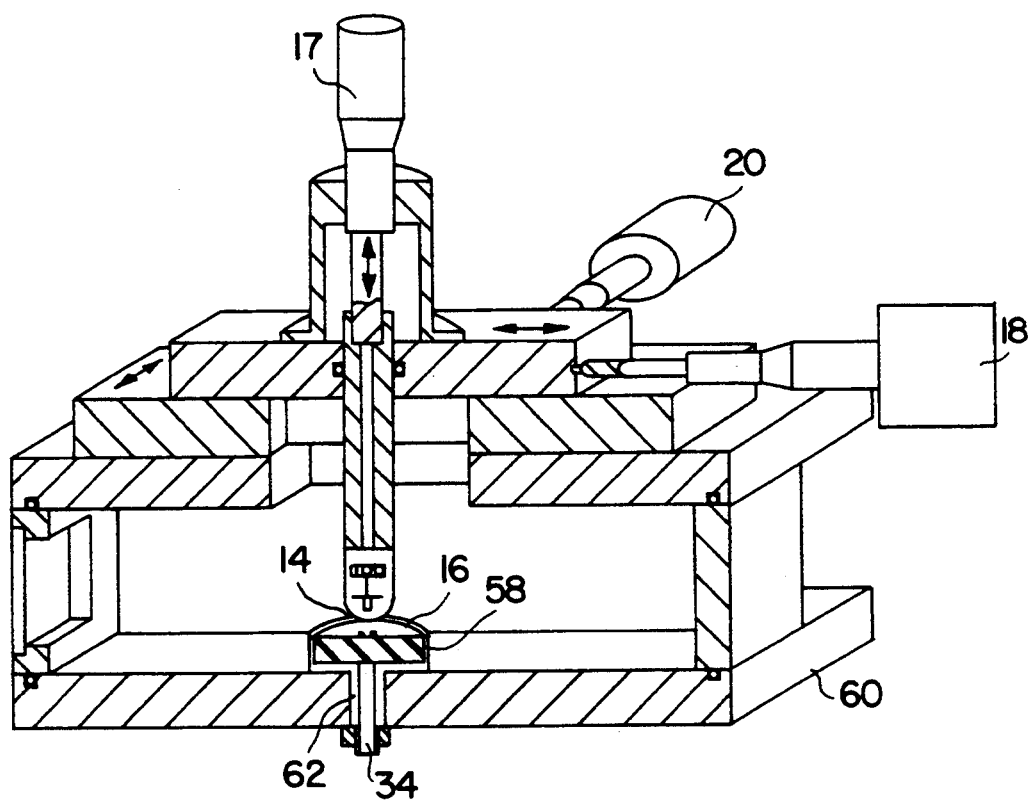
FIG. 2 shows a sectional view of the measuring system of the apparatus according to FIG. 1.

FIG. 2 shows a possible measuring system in section. In the embodiment therein shown sheet-form samples 16 are used, which are mounted in an insulated, cup-shaped holder 58 on a baseplate 60. The baseplate 60 is provided with an insulating passageway 62 for the line 34, which electrically connects the metal part of the sample with the differential amplifier 36.

Figure 3:
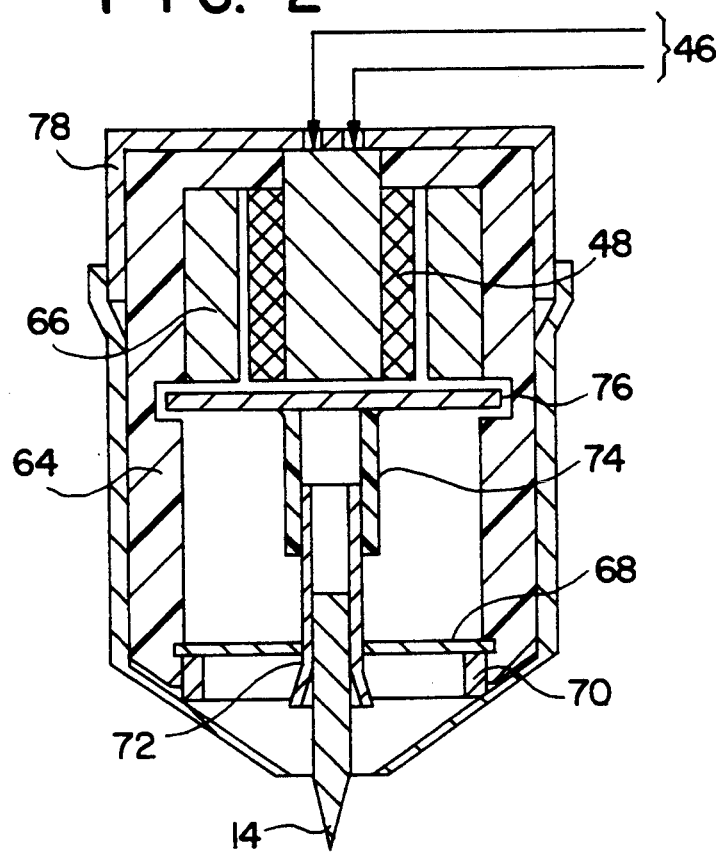
FIG. 3 shows an enlarged sectional view of a measuring head of the measuring system according to FIG. 2.

The measuring head 12, shown, on a larger scale in FIG. 3, has a cup-shaped synthetic housing 64, in the upper end of which the magnet coil 48 and a permanent magnet 66 are arranged. In the lower end of the housing 64 a sheet-form membrane 68 is held by its circumference, and it is connected with a contact ring 70 in order to ground the membrane. The middle of the membrane has a hole, in which a tube-shaped, somewhat widened towards the exterior, holder 72 of gilded copper is fixed, which serves for holding the reference electrode 14. The inner end of the holder 72 is connected via a ceramic tube 74 with a soft-magnetic vibration armature plate 76.

The housing 64 and the reference electrode 14, with the exception of its tip, are surrounded by a magnetic shield in the form of a mantle 78 of a highly permeable magnetic material, which is grounded and also provides capacitive shielding.

The described apparatus works in the following manner: The a-c voltage generator 42 of the amplifier 40 is tuned to the resonance frequency of the vibrating system 14-72-68-74-76 which includes the reference electrode 14, so that the magnet coil 48 is excited at the resonance frequency of this system. The permanent magnet core 66 acts to ensure that the armature 76 is driven at the excitation frequency of the magnet coil (and not at twice this frequency).

The tip of the vibrating needle-shaped reference electrode 14 is moved toward the surface of the coating of the sample 16 by means of the micrometer screw 17, until an output signal of sufficient amplitude arises at the line 34. This output signal is amplified in a frequency dependent manner in the lock-in amplifier; i.e., only those components of the output signal are amplified whose frequency corresponds with the frequency of the internal reference voltage which is delivered from the a-c voltage generator 42. The lock-in amplifier 40 delivers a unipolar voltage proportional to the amplified output signal, which unipolar voltage is: integrated by the integrator 50. The voltage U produced by the integrator 50 is led to the reference-signal input of the differential amplifier 36 as well as to the computer 24 as a measurement signal.

In the balanced condition of the operating cycle (amplitude of the amplified output signal equal to zero) the measurement signal U corresponds to the corrosion potential between the grounded reference electrode 14 and the coated, conductive boundary surface underneath the coating in the sample. The corresponding conductive loop for this runs from the reference electrode 14 via ground, an input resistance 80 (shown in broken lines) of the differential amplifier 36, the line 34 and the metallic part of the sample 16 to its surface under investigation. As is known, all contact potentials are canceled out with the exception of the corrosion potential between the reference electrode 14 and the coated surface of the sample which lies opposite to it.

The spatial resolution is the greater the smaller the radius of the tip of the reference electrode, and is essentially limited by the stray capacitance between the flanks of the reference electrode which border the tip and the surface of the sample. The influence of this stray capacitance can best be eliminated by utilizing those components of the capacitance signal used for measurement whose frequency is double the vibration frequency of the reference electrode. This may be explained as follows: The capacitance between the reference electrode 14 and the sample 16 is proportional to 1/d, where d is the distance between the reference electrode and the surface of the sample. When the distance d changes sinusoidally as a result of the vibration of the reference electrode 14, the course of the change in capacitance for those parts of the reference electrode, such as the flanks, which are relatively far from the sample surface, are very similar to a sine function. On the other hand, the course of the capacitance for very small values of d (and hence for the tip of the reference electrode 14) deviates strongly from that of a sine function, since at very small values of d the capacitance rises extra-proportionally.

The a-c current flowing between the reference electrode and ground is given by the derivative of the function 1/d. Thus, $i = dQ/dt,$ where Q is the charge in the condenser, which is an inverse function of d. Consequently, for the flanks of the reference electrode there results a current corresponding to a cosine function with the same frequency if as the fundamental vibration of the reference electrode. The current which is caused by the tip of the reference electrode exhibits on the other hand a completely different type of relationship. Since the course of the capacity between the tip of the reference electrode and the sample deviates extremely from that of a sine function, the measurement current also does not have a sine-form course but rather a complex form, which nevertheless can be approximated by superimposing a sine function of frequency if and a sine function of frequency 2f. The 2f component of the current (and hence the component of the doubled vibration frequency of the reference electrode) is the greater, the smaller the distance between the tip of the reference electrode and the sample surface.

The component of the current whose frequency is equal to the vibration frequency 1f of the reference electrode is thus caused essentially by the flanks of the reference electrode and only to a small degree by the tip of the reference electrode. If the selection in the lock-in amplifier 40 is carried out on the basis of the reference electrode vibration frequency 1f, the lateral resolution is relatively small (e.g. 100 μm) on account of the spurious capacitance of the flanks of the reference electrode; however, the sensitivity of the potential measurement is large, since the signals are correspondingly large because of the large surfaces of the flanks of the reference electrode.

On the other hand, if the selection of the measurement signal in the lock-in amplifier is carried out at 2f (i.e. the first harmonic of the vibration frequency of the reference electrode) the spatial resolution is very much better (thus for example 10 μm), since the component of the current whose frequency is equal to twice the vibration frequency of the reference electrode is caused exclusively by the tip of the reference electrode. The sensitivity of the potential measurement is in this case however less, since the surfaces of the needle tip is vanishingly small.

An analysis at the doubled vibration frequency 2f has moreover the additional advantage that electromagnetic noise caused by the magnet coil, whose frequency is 1f, are to a large extent eliminated.

The apparatus according to the invention makes it possible to ascertain corrosion potentials through an insulating dielectric, such as a polymer coating, with high spatial resolution. The surface to be investigated is scanned by suitable XY movement of the reference electrode with respect to the sample surface by means of step motors 18 and 20.

If a polymer film coating is undermined by water emanating from a local injury or damage, whereby the thickness of the water film may amount to only a few monolayers, the electrode potential of the now newly formed metal/water phase boundary changes substantially with respect to the previously existing metal/polymer boundary. This advancing undermining can easily be pursued with the aid of the high-resolution Kelvin probe. The delamination front is characterized by a potential jump, and the negative corrosion potentials correspond to the delaminated places whereas the positive potentials correspond to the still intact interface. By measurement of the advancing potential jump, one can easily ascertain the delmaination rate. Even local corrosion under an intact coating can be easily and unambiguously ascertained, since Chose regions at which the surface is corroded and the adhesion between metal and coating is lost clearly exhibit more negative potentials than such interfaces with good contact between metal and coating.

The needle-shaped reference electrode 14 consists in the described embodiment of a chromium-nickel alloy, at the front end of which a very sharp point was constructed by etching. However, other metals, such as tungsten, molybdenum, noble metals, etc. may also be used. By using a needle-shaped reference electrode running to a point, a spatial resolution of the order of 10 μm is obtainable. If no such high spatial resolution is required, an reference electrode with rounded or flattened front end can be used. With a given distance between the end of the probe and the metal surface, one can obtain higher output signals with such reference electrode configurations.

The vibrations of the reference electrode can also be produced by a piezoelectric element. Instead of the lock-in amplifier one can also use other frequency-selective circuits.

We claim:

1. A method of investigating the state of corrosion of a surface of a metal member provided with a coating which comprises a polymeric material, said method including the following steps: positioning a vibrating Kelvin type probe in spaced relationship at said coating, moving said Kelvin probe across said coated surface, and determining the potential between said metal and said probe during said movement.

2. The method as claimed in claim 1, wherein said metal is selected from the group consisting of iron, zinc and aluminum and other metals of similar reactivity.

* * * * *